United States Patent [19]

McMichael et al.

[11] Patent Number: 5,948,768
[45] Date of Patent: *Sep. 7, 1999

[54] TREATMENT OF OTITIS MEDIA BY SUBLINGUAL ADMINISTRATION OF DNA

[75] Inventors: John McMichael, Delanson, N.Y.; Michael Allen, Sacramento, Calif.

[73] Assignee: Milkhaus Laboratory, Delanson, N.Y.

[ * ] Notice: This patent is subject to a terminal disclaimer.

[21] Appl. No.: 09/123,800

[22] Filed: Jul. 28, 1998

Related U.S. Application Data

[63] Continuation-in-part of application No. 09/037,895, Mar. 10, 1998, which is a continuation-in-part of application No. 08/755,092, Nov. 22, 1996, Pat. No. 5,726,160, which is a continuation of application No. 08/421,232, Apr. 13, 1995.

[51] Int. Cl.$^6$ .............................. A01N 43/04; A61K 31/70
[52] U.S. Cl. ................................. 514/44; 536/22.1; 514/2; 514/47; 514/50; 424/9.2
[58] Field of Search ................................. 514/44, 2, 47, 514/50; 536/22.1; 424/9.2

[56] References Cited

U.S. PATENT DOCUMENTS

| | | | |
|---|---|---|---|
| 5,240,846 | 8/1993 | Collins et al. | 435/240.1 |
| 5,292,498 | 3/1994 | Boucher, Jr. | 424/45 |
| 5,420,116 | 5/1995 | Puchelle et al. | 514/47 |
| 5,470,838 | 11/1995 | von Borstel et al. | 514/50 |
| 5,726,160 | 3/1998 | McMichael | 514/44 |

FOREIGN PATENT DOCUMENTS

| | | |
|---|---|---|
| WO 92/11016 | 7/1992 | WIPO . |
| WO 93/12240 | 6/1993 | WIPO . |
| WO 94/23048 | 10/1994 | WIPO . |
| WO 95/25800 | 9/1995 | WIPO . |
| WO 96/32138 | 10/1996 | WIPO . |
| WO 96/40059 | 12/1996 | WIPO . |
| WO 97/05195 | 2/1997 | WIPO . |

OTHER PUBLICATIONS

Canonico, A.E. et al., "Expression of a CMV Promoter Driven Human α–1 Antitrypsin Gene in Cultured Lung Endothelial Cells and in the Lungs of Rabbits," *Clin. Res.*, 39(2): 219A (1991).

Ledley, F.D., "Non–viral gene therapy," *Current Opinion in Biotechnology*, 5: 626–636 (1994).

Ledley, F.D., "Nonviral Gene Therapy: The Promise of Genes as Pharmaceutical Products," *Human Gene Therapy*, 6: 1129–1144 (Sep., 1995).

Rosenfeld, M.A. et al., "Adenovirus–Mediated Transfer of a Recombinant α1–Antitrypsin Gene to the Lung Epithelium in Vivo," *Science*, 252: 431–434 (Apr. 19, 1991).

Marshall, E., "Gene Therapy's Growing Pains," *Science*, 269: 1050–1055 (Aug. 25, 1995).

Alton, E.W.F.W. et al., "Noninvasive liposome–mediated gene delivery can correct the ion transport defect in cystic fibrosis mutant mice," *Chemical Abstracts*, 119(21):62 (Nov. 22, 1993) (Absract 217089w).

Flotte, T.R., et al., "Stable in vivo expression of the cystic fibrosis transmembrane conductance regulator with an adeno–associated virus vector," *Chemical Abstracts*, 120(5):229 (Jan. 31, 1994) (Abstract 46918e).

*Textbook of Respiratory Medicine*, John F. Murray, ed., W.B. Saunders Company, Harcourt Brace Jovanovich, Inc., Philadelphia, PA, p. 1038 (1988).

Klein, J.O. Clinical Infectious Diseases, vol. 19, pp. 823–833, 1994.

Berman, S. Pediatrics, vol. 96, No. 1, pp. 126–131, Jul. 1995.

Karver Ear, Nose and Throat disorders, vol. 25, No. 3, pp. 619–632, Sep. 1998.

Baker, Pediatric Annals, vol. 20, No. 11, pp. 591–593, 596–598, Nov. 1991.

Rosenfeld et al. Primary care, clinics in office practice, vol. 23, pp. 677–685, 1996.

Dagan et al. Ear, Nose and Throat Journal, vol. 77, pp. 16–19, Jun. 1998.

*Primary Examiner*—Deborah Crouch
*Assistant Examiner*—Michael C. Wilson
*Attorney, Agent, or Firm*—Marshall, O'Toole, Gerstein, Murray & Borun

[57] ABSTRACT

Methods for treating symptoms of otitis media in a patient, are presented. Methods comprise administering an effective amount of DNA to a subject in a manner so as not to effect gene transfer.

6 Claims, No Drawings

5,948,768

TREATMENT OF OTITIS MEDIA BY SUBLINGUAL ADMINISTRATION OF DNA

This application is a continuation-in-part of U.S. patent application Ser. No. 09/037,895 filed Mar. 10, 1998 which is a continuation-in-part of U.S. patent application Ser. No. 08/755,092 filed Nov. 22, 1996, issued Mar. 10, 1998 as U.S. Pat. No. 5,726,160 which is a continuation of U.S. patent application Ser. No. 08/421,232 filed Apr. 13, 1995.

FIELD OF THE INVENTION

The present invention relates to methods for treatment of otitis media.

BACKGROUND OF THE INVENTION

The present invention relates generally to methods for treatment of pulmonary diseases and diseases associated with upper respiratory tract infection. Such diseases, including cystic fibrosis, emphysema, chronic bronchitis, sinusitis, and the common cold, have in common bronchial or sinus congestion, production of large amounts of sputum, and the possibility of secondary bacterial infection requiring antibiotic therapy.

Acute otitis media is a bacterial or viral infection in the middle ear which is usually secondary to upper respiratory tract infections and is most common in children. Microorganisms may migrate from the nasopharynx to the middle ear over the surface of the eustachian tube's mucous membrane or by propagating in the lamina propria of the mucous membrane as a spreading cellulitis or thrombophlebitis. Pain and hearing loss are the most common presenting complaints although fever, nausea, vomiting and diarrhea may occur in young children. Therapy for acute otitis media includes analgesics, decongestants and antibiotics. In addition, topical vasoconstrictors may be administered into the nasal cavity to improve eustachian tube function. Further, systemic sympathomimetic amines such as ephedrine sulfate may also be administered.

Serous otitis media (secretory otitis media) is an effusion in the middle ear resulting from incomplete resolution of acute otitis media or obstruction of the eustachian tube. Traditional therapy includes a trial of antibiotic therapy in case of bacterial infection. Such antibiotic therapy is effective in relieving eustachian tube obstruction due to bacterial infection and in sterilizing the middle ear. Systemic sympathomimetic amines may also improve eustachian tube function by their vasoconstrictive effects and antihistamines may relieve eustachian tube obstruction in allergic patients. Surgical therapies include myringotomy for aspiration of the fluid and for insertion of a tympanostomy tube which allows ventilation of the middle ear and ameliorates the eustachian tube obstruction. Alternatively, the middle ear may be temporarily ventilated with the Valsalva maneuver or politzeration.

Despite the efficacy of these approaches there remains a desire to avoid surgical intervention in cases of otitis media. Moreover, there exists a growing concern that the widespread use of antibiotics for treatment of otitis media in children promotes the development of antibiotic resistant bacteria. Accordingly, there remains a desire in the art for improved treatment of conditions associated with upper respiratory infections and pulmonary disorders including otitis media.

SUMMARY OF THE INVENTION

The present invention provides methods for treating symptoms of otitis media in a patient, comprising the step of administering in a manner so as not to effect gene transfer an effective amount of a polynucleic acid which is preferably DNA in a pharmaceutically-acceptable vehicle to a patient having otitis media.

Methods of the invention comprise administration to a patient suffering from otitis media including acute otitis media, serous otitis media and chronic otitis media an effective amount of a polynucleic acid which is preferably DNA. The polynucleic acid may be selected from the group consisting of single-stranded and double-stranded DNA and RNA and includes natural polynucleic acids as well as synthetic nucleic acids such as poly-dT. The preferred polynucleic acid for use according to the invention is double-stranded DNA which is preferably provided in an amount ranging from about 0.00012 mg to about 0.003 mg and is preferably formulated in a liquid vehicle and provided at a concentration of approximately 0.0006 mg as single drops. A preferred route of administration is sublingual, but other routes, such as subcutaneous, intravenous, intramuscular, and intrathecal are expected to work. In addition, topical administration in the form of ear drops is also expected to be useful according to the invention. DNA for use in the present invention may be prokaryotic DNA or eukaryotic DNA including DNA from sources such as calf thymus, E. coli and salmon testicles. The DNA may be formulated in a number of pharmaceutically-acceptable vehicles, including water, saline, albumin, and dextrose.

Additional aspects and advantages of the invention will become apparent upon consideration of the following detailed description thereof.

DETAILED DESCRIPTION OF THE INVENTION

The present invention provides methods for treating patients with symptoms of otitis media by administering to such patients a small amount of DNA in a manner so as not to effect gene transfer. Methods of the invention are also useful for treating upper respiratory infections and pulmonary disorders including but not limited to those involving congestion in patient,; having any disease in which mucus production is a symptom and are especially effective in treating diseases wherein viscous mucus or sputum is produced and becomes lodged in a patient's respiratory tract. In those cases, methods of the invention reduce production of DNA in a patient's mucus secretions and thereby render mucus less viscous, allowing for increased production away from the respiratory tract.

Methods according to the invention for treating otitis media have been tested in clinical trials with human patients using salmon or calf thymus DNA. In each case, patients are administered sublingual drops of DNA at a concentration of about 0.0006 mg DNA per drop. In general, no other therapy was conducted in any patient during the course of DNA therapy. No adverse side effects were observed in any patients. Drops of DNA may be administered at the appropriate concentration in doses of 1 to 10 drops per day as required by the patient. For each Example below, salmon testicle or calf thymus DNA (Sigma) was used.

The following Examples illustrate the methods of the invention with respect to treatment of pulmonary diseases and in particular with respect to the preferred methods of treating otitis media. Numerous improvements and further aspects of the invention are apparent to the skilled artisan upon consideration of the Examples which follow.

EXAMPLE I

Twenty-three year-old twin brothers presented with cystic fibrosis. Each had a history of hospitalizations for lung clearance and secondary infections diagnosed as being associated with their cystic fibrosis. Each patient began therapy with 1–2 drops (0.0006 mg/drop) of DNA sublingually per day. For almost two years since beginning DNA therapy, neither patient has been hospitalized. In addition, follow-up evaluations by physicians revealed a 30–45% increase in airflow in each patient Moreover, forced vital capacity, a common measure of lung capacity and the extent of mucus clearance in the lungs, increased from 60–90%. Finally, each of the brothers has gained weight and has shown increased expectoration.

After approximately one year of therapy, one of the brothers stopped taking the DNA drops. His condition steadily worsened as a result, with increased mucus viscosity, decreased forced vital capacity and reduced expectoration. That patient then began taking drops of DNA at the prescribed dose and immediately improved to the condition he was in prior to the time at which he stopped taking the drops.

EXAMPLE II

A 64-year-old female patient who suffered from emphysema and bronchitis, as diagnosed by her physician, was placed on a dose of 1 drop per day (0.0006 mg/drop) of DNA sublingually. Within one week, a follow-up evaluation revealed that her mucus production was less viscous and expectoration was increased.

EXAMPLE III

A 25-year-old female diagnosed with chronic upper respiratory illness was treated with methods according to the invention.'Previous antibiotic therapy was unsuccessful in treating her condition. She began with 1 drop of DNA (0.0006 mg/drop) sublingually four times per day. Within one day, she experienced an increase in expectoration and, after three days she was able to discontinue treatment, having been completely relieved of congestion. She has remained symptom free.

EXAMPLE IV

A 32-year-old female nurse presented with a severe upper respiratory infection and unproductive respiratory congestion. She was placed on 1 drop of DNA (0.0006 mg/drop) four times per day. Her congestion began to break up almost immediately. Expectoration was improved and the patient's illness resolved after 4.5 days and no congestion recurred.

EXAMPLE V

A 63-year-old woman presented with chronic sinusitis. Four drops of DNA per day were administered. After 3 months, the patient's mucus had thinned and her cough was more productive.

EXAMPLE VI

A 37-year-old female presented with unresolved respiratory congestion. Traditional therapy, including expectorants, failed to improve her condition. The patient was then prescribed four drops of DNA (0.0006 mg/drop) per day. After one day of treatment, her congestion was more productive and sinus drainage had begun where none was present prior to treatment according to the invention.

EXAMPLE VII

A 40-year-old woman with unproductive upper respiratory congestion was placed on 4 drops of DNA (0.0006 mg/drop) per day. Her congestion was more productive after one day and she continued to expectorate freely. In this case, therapy was supplemented with an over-the-counter expectorant.

EXAMPLE VIII

A 38-year-old woman with acute and chronic respiratory disease due to exposure to toxic corrosive materials was treated with methods according to the invention. Prior to such treatment, symptoms, including chronic rhinorrhea, chest congestion and chronic respiratory infections were treated with numerous courses of antibiotics without success. The patient began treatment with 0.5 cc Q.I.D. daily and was instructed to administer treatment up to 5–6 times daily if necessary.

Upon commencing treatment according to the invention, the patient was able to produce sputum almost immediately. Continued treatment has alleviated symptoms of chronic respiratory illness.

EXAMPLE IX

A 58-year-old woman diagnosed with a childhood history of asthma and persistent adult rhinitis and sinusitis presented for treatment. Physical examination indicated clear rhinorrhea, and 3+ red throat. Nasal spray and prednisone were prescribed for 7 days. That course of treatment resulted in mild improvement. However, the patient's cough was still unproductive. Therapy according to the invention was begun at 0.5 cc Q.I.D. Within 48 hours, the patient showed improvement in the form of a productive cough and sinus drainage.

EXAMPLE X

A 48-year-old woman with chronic sinusitis and bronchitis characterized by chronic head congestion, nasal obstruction, and coughing presented for treatment according to the invention. The patient was treated according to the invention with one drop per day of DNA (0.0006 mg/drop). Treatment resulted in an overt increase in sinus and chest drainage. Upon cessation of treatment according to the invention, the patient's condition regressed. Beginning therapy again caused a similar increase in drainage and relief of congestion as seen previously with treatment according to the invention.

The following examples report the results of treatment of subjects suffering from radiation induced mucositis with the DNA containing compositions of the invention.

EXAMPLE XI

According to this example, a subject suffering from radiation induced mucositis was treated with one drop of DNA (0.00006 mg/drop) sublingually four times per day. The subject experienced a 50% improvement with phlegm thickness and had less cough. Experimentation by the subject with dosage frequency revealed that administration of one drop alone was insufficient but that administration of three to four drops per day appeared to be optimal.

EXAMPLE XII

According to this example, a subject suffering from radiation induced mucositis was treated with one drop of DNA (0.0006 mg/drop) sublingually four times per day. While treatment with four drops per day did not provide subjective improvement an increase in dosage to ten drops per day may have resulted in less phlegm. The subject discontinued administration of DNA but restarted use later and reported thinning of phlegm. The formulation was later modified to include 2 units of streptolysin O per drop although it could not be determined if incorporation of streptolysin O improved the therapeutic results.

EXAMPLE XIII

According to this example, a subject suffering from radiation induced mucositis was treated with one drop of DNA (0.0006 mg/drop) sublingually four times per day with the result of a 50% improvement in phlegm thickness. In addition the subject noted that her sense of taste improved from nonexistent to normal.

The following examples report the results of treatment of three patients suffering with mild to moderate chronic obstructive pulmonary disease not characterized by aberrant mucous accumulation who were successfully treated with DNA containing compositions according to the methods of the invention.

EXAMPLE XIV

A 67 year-old male former smoker with a medical history of gout, hypertension, peptic ulcer and chronic obstructive pulmonary disease presented with shortness of breath during high humidity, walking up a half flight of stairs, walking in the yard and at night laying flat in bed. The subject suffered from minimal phlegm production which was white in color. The subject was being treated with allopurinol, Pepcid (famotidine), Slobid (theophylline), Calan (verapamil HCl), Accupril (quanapril HCl) and Albuterol Inhaler. A pre-study office spirometry showed moderate COPD with an Fev1% of 51.

The subject was treated with 1 drop of DNA (0.0006 mg/drop) sublingually four times per day. After fourteen days of treatment the subject reported that his overall dyspnea had improved from a subjective rating of a 10 to a 4. He was able to walk at the mall without shortness of breath where previously, he had to stop. A spirometry on day 16 showed no change but three months later with continued treatment according to the invention could ascend 13 steps where prior to treatment he had been unable to ascend only half as many steps without dyspnea. The subject was also able to decrease Albuterol administration from daily to 2–3 times weekly and eventually to once in four weeks and discontinue use of Slobid. The subjects wife reported that the subject's sleep is more restful and that she no longer hears wheezing at night.

EXAMPLE XV

A 71 year-old female with a medical history of hypertension, myocardial infarction, renal insufficiency, hiatal hernia, spinal stenosis, hyperlipidemia and chronic obstructive pulmonary disease presented with shortness of breath while cooking meals, walking 17 steps, carrying laundry, vacuuming, making her bed, walking to the car, and in the mall. She also complained of minimal phlegm. She was undergoing treatment with medications including Cardizem CD (ditiazem HCl), Vasotec (enalaprilat), Zocor (simvastatin), Ogen (estropripate), Zantac (ranitidine HCl), Toprol (metoprolol succinate), Nitroglycerine patch, LorTab (hydrocodone bitartrate and aspirin), and a sleep agent as required. Upon examination, she had mild anterior wheezing and a pre-study office spirometry showed an Fev1of 70.

The subject was treated with 1 drop of DNA (0.0006 mg/drop) sublingually four times per day. After seven days of treatment the subject reported no improvement but fourteen days of treatment reported that she could walk in the mall without shortness of breath and was vacuuming and making her bed without needing to stop and rest. A repeat spirometry after fourteen days showed an Fev1% of 78, an 11% improvement from the pre-study result. The subject's condition continued to improve except when she decreased the treatment schedule to once per day and her shortness of breath returned. After increasing back to treatment four times daily her dyspnea resolved to the extent that she was able to discontinue her use of a Serevent (Glaxo) aerosol inhaler after four months.

EXAMPLE XVI

A 76 year-old female with a medical history of hypertension, arrhythmia, hypercholesterolemia, chronic obstructive pulmonary disease (for at least ten years) and anxiety presented with dyspnea after climbing one flight of stairs, exertional dyspnea and cough and with minimal phlegm. The subject was being treated with Normodyne (labetalol HCl), Procardia (nifedipine), Persantine (dipyridamole), Zocor (simvastatin), Atrovent Inhaler (ipratropium bromide) and Xanax (aprazolam). Upon examination, she had moderately decreased lung sounds with normal blood pressure. A spirometry conducted ten years previously showed an Fev1% of 73 (normal) with diminished mid flow rates suggesting early COPD.

The subject was treated with 1 drop of DNA (0.0006 mg/drop) sublingually twice daily and after one month of treatment had less coughing and diminished wheezing at home when in bed. A spirometry after almost two months of treatment showed an Fev1% of 65. The subject continued to report subjective improvement and stopped administration of Atrovent. After four months wheezing was nearly gone and her cough was less than prior to treatment according to the invention.

EXAMPLE XVII

According to this example, several asthma patients, were treated by daily administration of at least one drop of DNA (0.0006 mg/drop) derived from either salmon sperm or bovine sources. Follow-up evaluation of those subjects showed decreased viscosity and volume of sputum. In addition, the salmon sperm DNA was found to have therapeutic activity equivalent to that of the bovine derived DNA.

EXAMPLE XVIII

According to this example, a 56 year old non-smoker with chronic obstructive pulmonary disease/emphysema secondary to asbestosis and total disability due to pulmonary insufficiency was treated by sublingual administration of at least one drop of DNA (0.0006 mg/drop) four times daily. After a few weeks of treatment the subject reported feeling "dramatically better"and "not out of breath." The subject has since reduced them frequency of treatment to one drop daily.

EXAMPLE XIX

According to this example, the sublingual administration of one drop of DNA (0.0006 mg/drop) provided almost immediate relief of symptoms of respiratory disorders caused by chemical or environmental sensitivities. The therapy was tested on at least a dozen individuals including children and adults and was successful in all cases.

In the following examples, administration of DNA derived from either salmon testicles or calf thymus (Sigma)

was found to be useful in treatment of otitis media with rapid and reproducible responses.

EXAMPLE XX

According to this example, a five year old female presented with severe recurrent otitis media in the right ear with bulging of the tympanic membrane. The subject was treated with sublingual administration of one drop of DNA (0.0006 mg/drop) four times daily for seven days. When the subject was rechecked two days later the mother reported the child's temperament and energy improved the first evening. She went to school the next day. On exam, she had an injected tympanic membrane, but the bulging was gone. Significantly, this subject has been treated for OM numerous times in the past with antibiotics.

Roughly nine days after termination of treatment according to the invention the subject developed recurrent pain in the left ear with a fever of 101° F. Her mother did not contact the physician but administered the DNA composition of the invention again with success. She went to school the next day. The patient presented again Apr. 2, 1998 with recurrent otitis media in the right ear. She was again treated by sublingual administration of the DNA composition of the invention resulting in rapid sense of pain relief, temperature resolution and improved overall well being.

EXAMPLE XXI

According to this example, a nine year old female presented with a plugged feeling in the right ear, fever of 100° F. and minimal pain. A right otitis media was diagnosed. The subject was treated with sublingual administration of one drop of DNA (0.0006 mg/drop) four times daily. The first night of treatment, the child slept well, the pain left and she went to school the next day. Four days later the redness and fluid were less. The mother reported that usually with otitis media and antibiotic treatment, her child had 2–3 restless nights and usually missed 2–3 days of school. In the case of treatment according to the invention she went to school the next day.

EXAMPLE XXII

According to this example, a five year old female presented with acute otitis media in which she had a fever, was whining and was restless. The mother gave her one dose of a plant-derived homeopathic remedy in the late afternoon. It helped some, but later that night, severe pain recurred. The subject was treated with a single sublingual administration of one drop of DNA (0.0006 mg/drop). No further doses were given. The child went to pre-school the next day. The ear was checked several times the next three weeks and gradually it returned to normal.

EXAMPLE XXIII

According to this example, a seventeen month old male presented with recurrent serous otitis media. The subject was treated with sublingual administration of one drop of DNA (0.0006 mg/drop) four times daily for one month. There occurred complete resolution of the fluid.

EXAMPLE XXV

According to this example, a three year old presented with recurrent serous otitis media. The subject was treated with sublingual administration of one drop of DNA (0.0006 mg/drop) hourly until pain was eliminated. The subject was then treated four times daily for one week and had a complete resolution of symptoms.

EXAMPLE XXV

According to this example, a two year old female presented with bilateral otitis media with pain. The subject was treated with sublingual administration of one drop of DNA (0.0006 mg/drop) hourly until the pain was relieved and then one drop four times daily for one week and had a complete resolution of symptoms.

EXAMPLE XXVI

According to this example, a ten month old male presented with bilateral serous otitis media and eustachian tube dysfunction. The subject was treated with sublingual administration of one drop of DNA (0.0006 mg/drop) four times daily for one month. Reevaluation after one month showed normal eustachian tubes.

EXAMPLE XXVII

According to this example, a fourteen month old male presented with recurrent bilateral serous otitis media for which surgery to insert tympanostomy tubes into the eustachian tubes was originally recommended. The subject was treated with sublingual administration of one drop of DNA (0.0006 mg/drop) four times daily. Evaluation one and two months later revealed incomplete resolution of fluid but evaluation three months later revealed complete elimination of fluid. Five months after initiation of therapy bilateral otitis media recurred but resumption of therapy with the DNA drops resulted in a complete resolution.

The invention has embodiments has been described in terms of its preferred embodiments and is only intended to be limited by the scope of the following claims.

What is claimed is:

1. A method for treating symptoms of otitis media, comprising the step of:

sublingually administering in a manner so as not to effect gene transfer an effective amount of DNA in a pharmaceutically-acceptable vehicle to a patient having otitis media wherein said method results in improvement of one or more symptoms selected from the group consisting of fever pain and fluid retention associated with otitis media.

2. The method according to claim 1 wherein said DNA is administered sublingually in the form of a liquid drop.

3. The method according to claim 1 wherein said vehicle is selected from the group consisting of water, saline, albumin, or dextrose.

4. The method according to claim 1 wherein said effective amount of DNA is from about 0.00012 mg to about 0.003 mg DNA.

5. The method according to claim 1 wherein said effective amount of DNA is about 0.0006 mg of DNA.

6. The method according to claim 1 wherein said patient is a human.

* * * * *